United States Patent
Roney, Jr. et al.

(10) Patent No.: US 7,026,811 B2
(45) Date of Patent: Apr. 11, 2006

(54) METHODS AND APPARATUS FOR EDDY CURRENT INSPECTION OF METALLIC POSTS

(75) Inventors: Robert Martin Roney, Jr., Schoharie, NY (US); Thomas Francis Murphy, Scotia, NY (US)

(73) Assignee: General Electric Company, Schenectady, NY (US)

( * ) Notice: Subject to any disclaimer, the term of this patent is extended or adjusted under 35 U.S.C. 154(b) by 168 days.

(21) Appl. No.: 10/805,013

(22) Filed: Mar. 19, 2004

(65) Prior Publication Data

US 2005/0206374 A1 Sep. 22, 2005

(51) Int. Cl.
*G01N 27/82* (2006.01)

(52) U.S. Cl. ........... 324/242; 324/201; 324/202; 324/207.11; 324/207.21; 324/209; 324/219; 324/228; 324/232; 324/234; 324/235; 324/238; 324/239; 324/241; 324/243; 324/257; 324/260; 324/261; 324/262

(58) Field of Classification Search ........... 324/242, 324/219, 207.11, 201, 202, 2, 207.13–207.15, 324/207.21, 209, 228, 232, 234–235, 238–239, 324/241–243, 260–262, 257
See application file for complete search history.

(56) References Cited

U.S. PATENT DOCUMENTS

| | | | |
|---|---|---|---|
| 3,768,011 A * | 10/1973 | Swain | 324/117 R |
| 4,139,822 A | 2/1979 | Urich et al. | |
| 4,644,274 A | 2/1987 | Casarcia | |
| 4,741,203 A * | 5/1988 | Willaman et al. | 73/116 |
| 5,140,264 A | 8/1992 | Metala et al. | |
| 5,315,234 A * | 5/1994 | Sutton et al. | 324/242 |
| 5,345,514 A | 9/1994 | Mahdavich et al. | |
| 5,442,286 A * | 8/1995 | Sutton et al. | 324/242 |
| 5,659,248 A | 8/1997 | Hedengren et al. | |
| 5,903,147 A | 5/1999 | Granger, Jr. et al. | |
| 6,019,001 A * | 2/2000 | Schreiner et al. | 73/640 |
| 6,339,326 B1 | 1/2002 | Trantow | |
| 6,339,331 B1 | 1/2002 | Ruzzo | |
| 6,469,503 B1 | 10/2002 | Trantow et al. | |
| 6,541,955 B1* | 4/2003 | Landre | 324/127 |
| 6,545,467 B1 | 4/2003 | Batzinger et al. | |
| 6,812,697 B1* | 11/2004 | McKnight et al. | 324/262 |

* cited by examiner

*Primary Examiner*—Michael Tokar
*Assistant Examiner*—Diane E. Jones
(74) *Attorney, Agent, or Firm*—Armstrong Teasdale LLP

(57) ABSTRACT

An apparatus for inspecting a metallic post contoured in a single dimension for defects. The apparatus has a clamp having at least one jaw with a surface conforming to the contour to the metallic post. The conforming jaw or jaws also have a plurality of eddy current coils and the probe has at least one sensor configured to sense at least one of position or motion.

22 Claims, 4 Drawing Sheets

METHODS AND APPARATUS FOR EDDY CURRENT INSPECTION OF METALLIC POSTS

BACKGROUND OF THE INVENTION

This invention relates generally to methods and apparatus for eddy current inspection of metallic posts contoured in one direction, such as turbine engine dovetail posts.

At least one known gas turbine rotor assemblies include a rotor wheel to which a plurality of blades are coupled. The blades extend radially outward from a platform that extends between an airfoil portion of the blade and a dovetail portion of the blade. The dovetail portion of the blade has at least one pair of dovetail tangs that couples each rotor blade to a complementary dovetail slot in an outer rim of the rotor wheel. Each of these slots is formed at an angle, called a skew angle, relative to the turbine center line.

Dovetail slots in the outer rim are sized to receive the dovetail tangs of the dovetail portion of the blade. The dovetail slot has at least one thick corner and one acute corner. The acute corners in a dovetail slot represent a natural geometric stress concentration, which is accentuated by the dovetail slot skew angle and the operational duty of the equipment. If cracks initiate during service, they may become susceptible to high cycle fatigue. Over time, continued operation with dovetail slots may result in blade release. If cracks are found near these locations through normal rotor maintenance, the affected rotors may be either retired from service or repaired.

At least one known method for inspecting gas turbine dovetail slots uses a single hand-held eddy current probe. Inspectors move a hand held probe over an area of a dovetial slot to be inspected. During manual probing, a technician watches an oscilloscope to look for defect signals. Use of this type of probe makes it difficult to provide complete coverage of the dovetail slot and slot bottom during an inspection and to record collected data for further evaluation or comparison. Also, it is difficult for a small, single coil to traverse the geometry of the dovetail, thereby making it necessary to complete multiple passes to test a single dovetail as well as resulting in a relatively low probability of defect detection. Because of the large amount of time required to perform inspections using a single hand-held probe, it is difficult and expensive to perform a complete inspection.

U.S. Pat. No. 5,659,248 to Hedengren et al. describes an eddy current surface measurement array structure for complete coverage of an underlying inspection surface without requiring mechanical scanning. A three dimensional array of eddy current sense elements is organized as a plurality of layers of two-dimensional sub-arrays. The sub-arrays, although in different layers, are essentially identical in configuration and are staggered such that the sense elements of one layer provide at least partial coverage of portions of the inspection surface not covered by the sense elements of another layer. The sense elements are disposed in a layered flexible structure fabricated employing high density interconnection fabrication techniques or other photolithographic techniques. Static (electronic) scanning is employed, by individual layer and by row and column within each layer, to form a two-dimensional image of the inspection surface.

U.S. Pat. No. 6,545,467 B1 to Batzinger et al. discloses that eddy current inspection of a contoured workpiece is performed by forming a backing piece of flexible, resiliently yieldable material with a contoured exterior surface conforming in shape to the workpiece contoured surface. The backing piece is preferably cast in place so as to conform to the workpiece contoured surface. A flexible eddy current array probe is attached to the contoured exterior surface of the backing piece such that the probe faces the contoured surface of the workpiece to be inspected when the backing piece is disposed adjacent to the workpiece. The backing piece is then expanded volumetrically by inserting at least one shim into a slot in the backing piece to provide sufficient contact pressure between the probe and the workpiece contoured surface to enable the inspection of the workpiece contoured surface to be performed.

Although the apparatus and methods of Hedengren et al. and Batzinger et al. are effective, they are relatively large and expensive to produce and require special shimming to maintain contact with a surface.

BRIEF DESCRIPTION OF THE INVENTION

Some configurations of the present invention therefore provide a method for inspecting a metallic post that is contoured in a single dimension for defects. The method includes clamping an eddy current probe having at least one jaw with a surface conforming to the contour to the metallic post. The conforming jaw or jaws have a plurality of eddy current coils and a sensor configured to sense at least one of position or motion. The eddy current probe is operated while clamped to produce data relating to structural integrity of the metallic post, and moved along the post while clamped and while sensing the structural integrity data and movement or position (or both) of the eddy current probe.

Furthermore, some configurations of the present invention provide a method for inspecting a metallic post that is contoured in a single dimension for defects. This method includes clamping an eddy current probe having at least one jaw with a surface conforming to the contour to the metallic post. The conforming jaw or jaws also have a plurality of eddy current coils, and the probe has at least one rubber wheel configured to move the eddy current probe along the metallic post. The eddy current probe is operated while clamped to produce data relating to structural integrity of the metallic post. The eddy current probe is moved along the post using the rubber wheel while clamped and while sensing said structural integrity data.

Some configurations of the present invention provide an apparatus for inspecting a metallic post contoured in a single dimension for defects. The apparatus has a clamp having at least one jaw with a surface conforming to the contour to the metallic post. The conforming jaw or jaws also have a plurality of eddy current coils and the probe has at least one sensor configured to sense at least one of position or motion.

In various configurations, the present invention provides an apparatus for inspecting a metallic post contoured in a single dimension for defects. The apparatus has a clamp having at least one jaw with a surface conforming to the contour to the metallic post. The conforming jaw or jaws also have a plurality of eddy current coils and the probe has at least one motorized wheel configured to accurately move the clamp along the metallic post while clamped thereto.

It will thus be appreciated that configurations of the present invention can be used to provide a complete inspection of critical areas of a dovetail post and spacer of a turbine engine, and for dovetail post inspections in which the probe passes over a dovetail post rather than a thru-slot. Use of configurations of the present invention can result in a decrease in inspection time, thereby allowing inspections to be performed during a hot gas path outage. Configurations of the present invention can also be performed with a high degree of accuracy with reliable probability of detection. Moreover, inspections can be automated and data obtained from an inspection can be archived for future comparison.

DETAILED DESCRIPTION OF THE INVENTION

Figure 1:
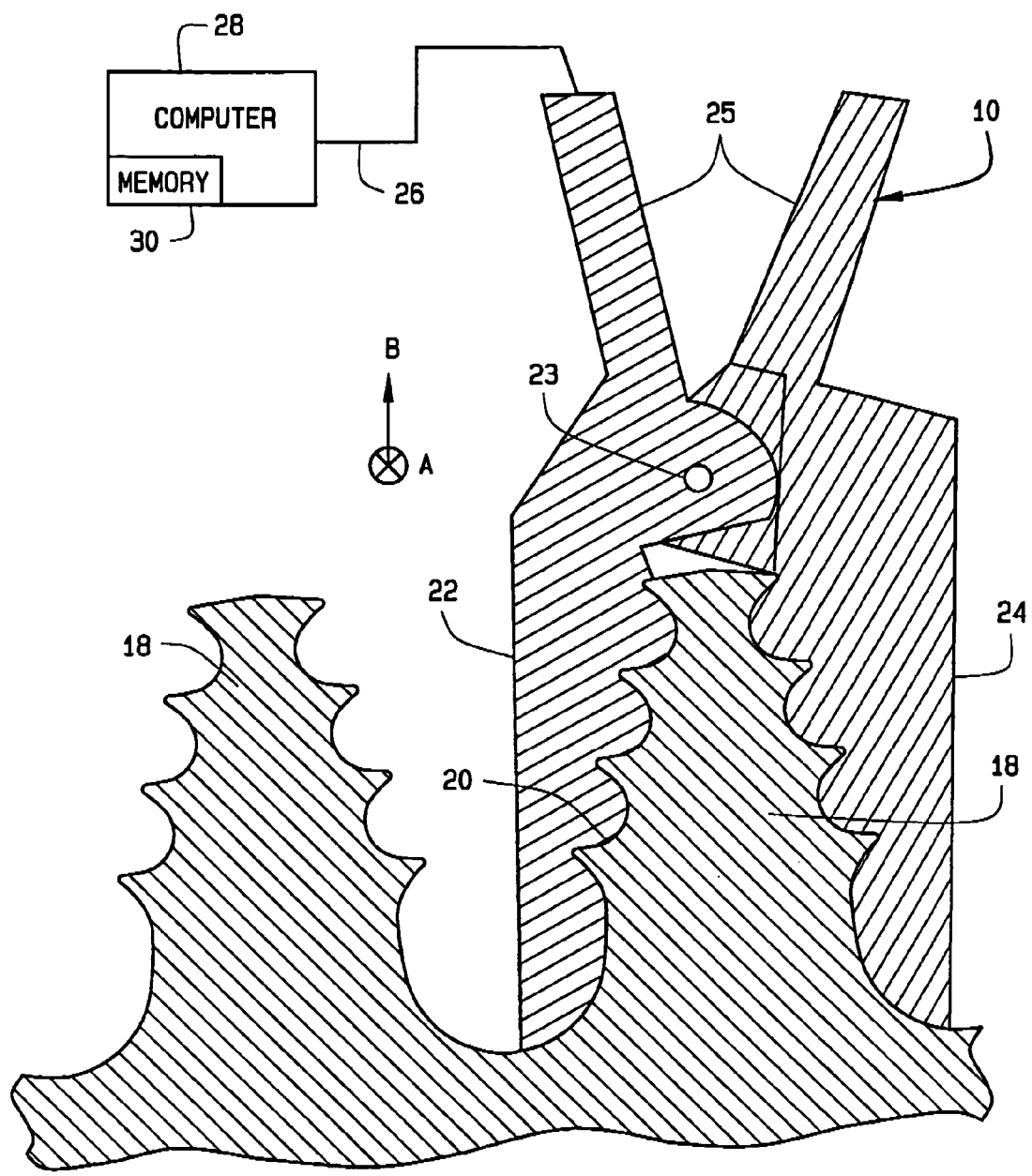
FIG. 1 is an axial sectional view of the rim of a turbine rotor wheel showing a pair of dovetail posts having contoured facing surfaces forming a dovetail slot therebetween to be inspected for the presence of cracks, and an eddy current probe configuration of the present invention placed on one of the dovetail posts positioned for the inspection.
Figure 2:
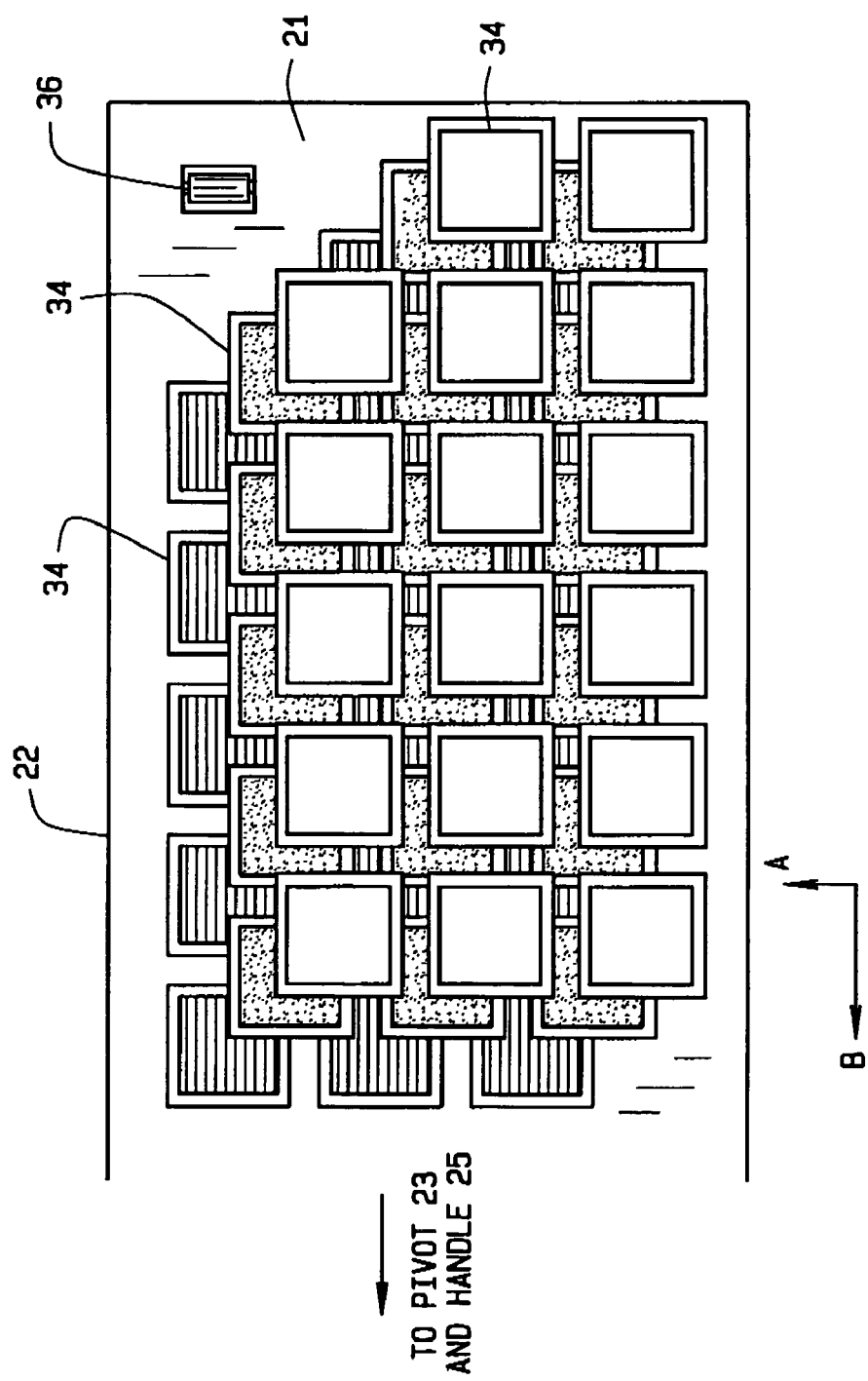
FIG. 2 depicts in plan view and in highly schematic fashion an eddy current surface measurement array including three layers of two-dimensional staggered subarrays and a position sensing element on a surface of a jaw of the eddy current probe configuration shown in FIG. 1. The plane of the illustration of FIG. 2 is perpendicular to the plane of the illustration of FIG. 1. Also, the surface has been flattened for simplicity of illustration, and does not show the contours present in the eddy current probe configuration illustrated in FIG. 1.

In some configurations of the present invention and referring to FIG. 1 and FIG. 2, an eddy current probe 10 is provided that has at least one jaw 22 or 24 that conforms to a shape of a metallic post 18 that is contoured in a single direction B, such as a radial direction. Post 18 is, for example, a dovetail post (and, if present, a spacer) of a turbine engine to be inspected, and has a constant profile in an axial direction. Eddy current probe 10 is clamped over metallic post 18 (and spacer if present) and moved across the surface 20 of post 18 as it is operated to produce relating to structural integrity of metallic post 18.

For the sake of simplicity, it will be assumed throughout the remainder of this description that metallic post 18 is a dovetail post of a turbine engine. It will be recognized, however, that the present invention can also be practiced in conjunction with other types of metallic posts.

In FIG. 1, dovetail post 18 has a constant cross-section as a function of axial position and extends a greater length in the axial direction than does eddy current probe 10. Eddy current probe 10 is moved to traverse the axial length of dovetail post 18 in a direction perpendicular to the plane of FIG. 1.

Eddy current probe 10 in some configurations comprises a pair of clamping jaws 22, 24, at least one of which (e.g., 22) includes a plurality of eddy current coils 34 on a surface or substrate 21 that faces surface 20 of post 18. Also, at least one of clamping jaws 22 or 24 includes at least one movement or position sensor 36. In some configurations, position sensor 36 can be a rubber wheel that provides controlled movement of eddy current probe 10 in the axial direction of dovetail post 18. The jaws may be spring-loaded to bias them with respect to a pivot 23 into position against surface 20 of post 18. Clamping is effected via handles 25, and movement in the axial direction along post 18 can also be effected manually, in some configurations, via handles 25. Coils 34 and position sensor 36 in some configurations are connected via a wired or wireless interconnection 26 to a computer 28 that includes memory 30. The memory may comprise any of several different types of storage elements and combinations thereof, and may include, for example, storage devices that write on fixed or removable media. Computer 28 is programmed to communicate with eddy current probe 10 and to receive and store data from eddy current probe 10 relating to its position and to structural integrity of post 18 for immediate and/or later analysis.

In some configurations and referring to FIG. 2, a plurality of eddy current coils 34 are operably arranged on, in, or under a surface 31 of at least one of jaws 22 or 24 in any suitable manner, for example, on a substrate affixed to surface 31. (Surface 31 is not flat as shown in FIG. 2. In fact, surface 31 has a contoured, dovetail shape, but to simplify the illustration, the curvature of surface 31 is not represented in FIG. 2.) Eddy current coils 34 may be arrayed as shown and manufactured as described in Hedengren et al., "Multilayer eddy current probe array for complete coverage of an inspection surface without mechanical scanning," U.S. Pat. No. 5,659,248, issued Aug. 19, 1997. For example, a flexible structure containing coils 34 can be manufactured and permanently adhered to surface 31 of jaw 22 and/or jaw 24. In other configurations, an array of coils 34 are embedded or supported under surface 31 of jaw 22 and/or jaw 24 so as to operatively sense defects in dovetail post 18. Coils 34 need not be arrayed rectangularly, and no particular arrangement or quantity of coils 34 (whether in one, two, or three dimensions) should necessarily be inferred from FIG. 2. However, coils 34 should be arrayed and present in sufficient number to provide complete sensing of the surface of a conforming dovetail post 18 when probe 10 is clamped thereon and moved in radial direction A over the full depth of dovetail post 18. (In FIG. 1, direction A is perpendicular to the plane of the illustration, i.e., into the paper.)

One or more encoders 36 are mounted in probe 10. Encoders 36 may be of any suitable type, electrical, mechanical, or optical, that can sense motion of probe 10 across dovetail post 18 when probe 10 is clamped thereon. For example, and not by way of limitation, encoder 36 in FIG. 2 can be an optical motion detector, or a slot can be provided for an encoder wheel 36 that contacts a surface of dovetail post 18. In the latter case, encoder wheel 36 rotates as probe 10 is moved, and electronically encodes a signal indicative of the direction and amount of movement that has occurred. Encoders 36 can be mounted in either of both of jaws 22 and 24, whether or not coils 34 are provided in the jaw in which encoders 36 are mounted. One or more encoder 36 is provided, and it is not a requirement that any encoder be on the same jaw 22 or 24 on which coils 34 are provided. For example, if coils 34 are provided on only one jaw 22 or 24, encoder 36 can be provided on the other jaw, so long as jaws 22 and 24 are mechanically coupled to enable coil 34 positions on one side of a post 18 to be determined from encoded position or motion data from encoder 36.

Encoded position or movement information is sent to computer 28 in some configurations as eddy current probe 10 and dovetail post 18 are moved relative to one another and as coils 34 are operated as sensors to produce data relating to the structural integrity of post 18. A sufficient number of coils 34 in eddy current probe 10 are provided to ensure adequate overlap between passes.

The shape of eddy current probe 10 allows complete inspection of critical areas of dovetail post 18 and any spacer that is present. Moreover, as a result of having encoded position data available, it is not necessary that probe 10 have the same depth (i.e., extent along direction A) as dovetail post 18, making probe 10 smaller and more convenient to carry and transport, and less expensive to manufacture.

Eddy current probe 10 is clamped on dovetail post 18 and/or moved across the surface manually. In some configurations, the movement of eddy current probe 10 is motorized and under control of computer 28. In some configurations, rubber wheels are used at 36 to propel eddy current probe 10. Wheels 36 may also function as encoder wheels or be operated by a stepping motor (not shown) to accurately control the position of eddy current probe 10. After completion of one side of dovetail post 18, probe 10 is rotated 180 degrees (in configurations in which only one of jaws 22 and 24 are provided with coils 34). This process is repeated until all tests are completed. Collected data is analyzed to locate structural flaws. The collected data can be archived to CD-ROM or DVD or any other suitable storage medium.

Figure 3:
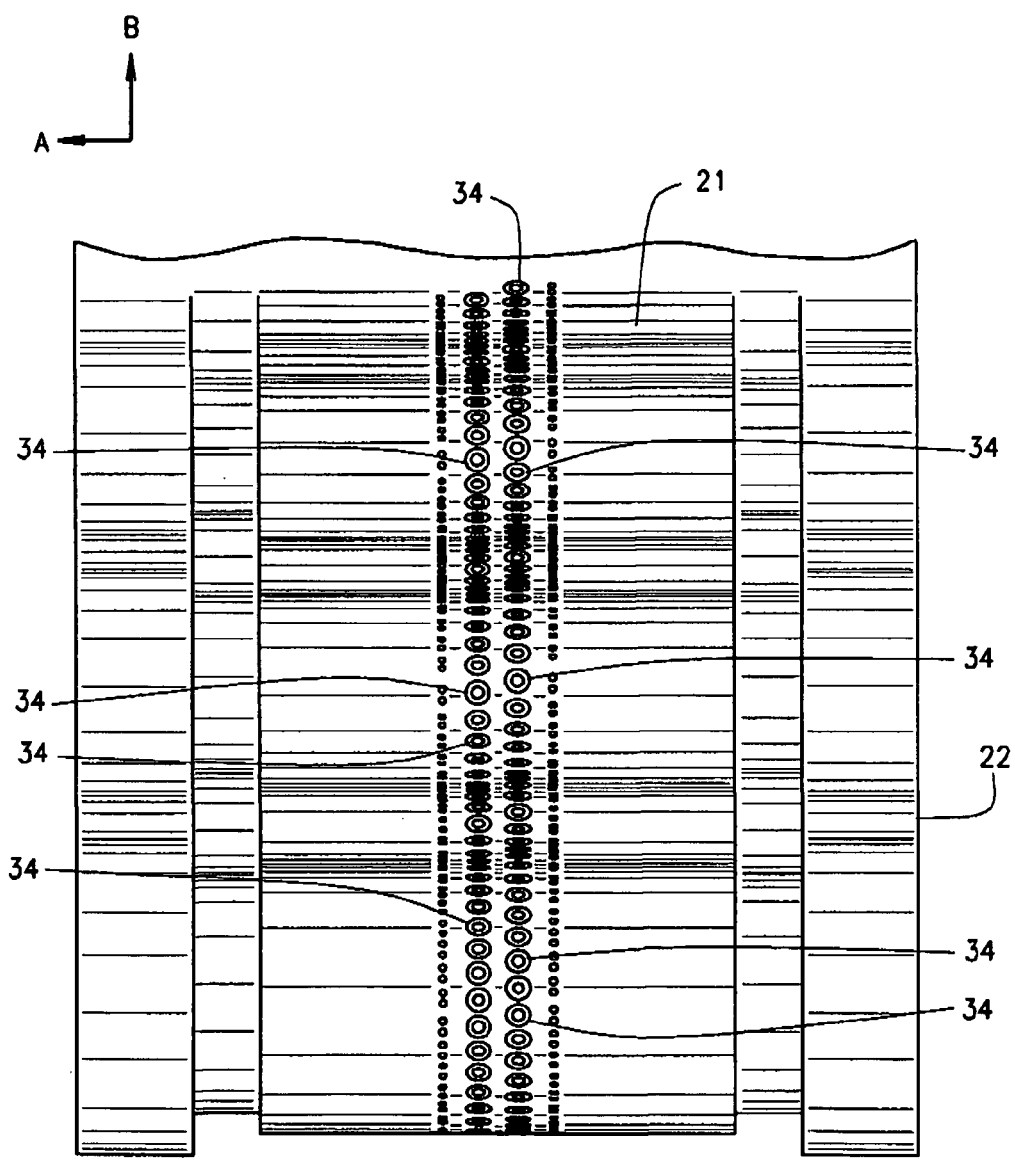
FIG. 3 is a drawing of another configuration of a surface of a jaw of an eddy current probe configuration such as that shown in FIG. 1. In this configuration, the contouring of the jaw is shown, and the handle is only partially shown.
Figure 4:
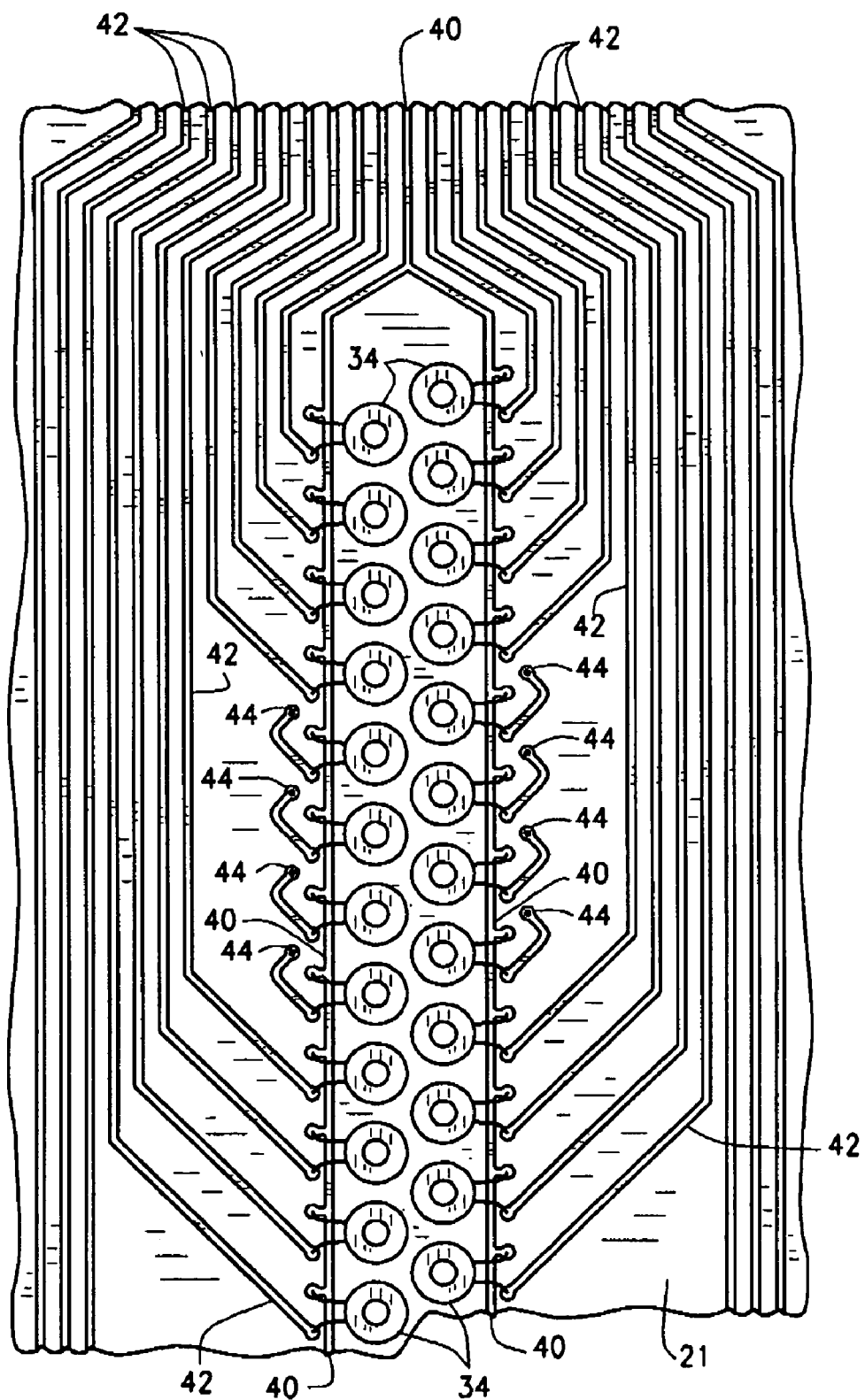
FIG. 4 is a partial view of a flexible, printed circuit substrate that can be used to cover the jaw of an eddy current probe configuration such as that shown in FIG. 3.

In another configuration and referring to FIG. 3 and FIG. 4, one or two rows of coils 34 are arranged on a substrate 21 that is affixed or otherwise attached to a surface of jaw 22 (and/or jaw 24) that conforms in shape to a post 18. (Motion sensor 36 is not shown in FIG. 3, but can be included with the opposite jaw, as a single motion sensor 36 on either jaw 22 or 24 is sufficient.) Not shown in FIG. 3, but shown in FIG. 4, are a plurality of electrical conductors on substrate 21 that are electrically coupled to coils 34. A common conductor 40 is electrically coupled to one end of the winding of each coil 34, and separate conductors 42 are provided for electrically coupling to the opposite end of the winding of each coil 34. In some configurations, a double-sided or multi-layer substrate 21 is provided and some conductors 42 are connected using vias 44 or other suitable interconnections to conductors on the other side or in another layer. Coils 34 and/or substrate 21 may be flexible, rigid or semi-flexible. In some flexible configurations, printed circuitry on flexible substrate 21 such as kapton or mylar, is used. Such configurations may be multi layered. In some rigid configurations, solenoid or pancake coils 34 are mounted or embedded on a rigid substrate 21 such as epoxy or any other suitable polymer, and at least one axis of symmetry is provided. In some semi-flexible configurations, solenoid or pancake coils 34 are mounted on a flexible substrate 21 such as mylar, rubber or kapton.

Inefficiency and indeterminate coverage of single coil inspection methods and apparatus are thus overcome by some configurations of the present invention that provide an eddy current array and mechanical probe that conforms to the shape of a metallic post, e.g., a gas turbine dovetail shape. Using such a probe, it is now possible and practical to handle larger amounts of information and cover much larger surface area in a single pass. Eddy current array probe configurations of the present invention allow for complete inspection of dovetail, spacer and slot bottom areas with a high degree of accuracy and in a short period of time. With one pass of the probe all features of one side of the dovetail can be interrogated, recorded and analyzed. The automated data can be archived to CD for future data comparison.

Configurations of the present invention can be used to provide a complete inspection of critical areas of a dovetail post and spacer of a turbine engine, as well as for dovetail post inspections in which the probe passes over a dovetail post rather than a thru-slot. Use of configurations of the present invention can result in a decrease in inspection time, thereby allowing inspections to be performed during a hot gas path outage. Configurations of the present invention can also be performed with a high degree of accuracy with reliable probability of detection. Moreover, inspections can be automated and data obtained from an inspection can be archived for future comparison.

While the invention has been described in terms of various specific embodiments, those skilled in the art will recognize that the invention can be practiced with modification within the spirit and scope of the claims.

What is claimed is:

1. A method for inspecting a metallic post that is contoured in a single dimension for defects, said method comprising:
   clamping an eddy current probe having at least one jaw with a surface conforming to the contour to the metallic post, said at least one jaw also having a plurality of eddy current coils and said probe further having a sensor configured to sense at least one of position or motion;
   operating the eddy current probe while clamped to produce data relating to structural integrity of the metallic post; and
   moving the eddy current probe along the post while clamped and while sensing said structural integrity data and at least one of movement or position of the eddy current probe.

2. A method in accordance with claim 1 further comprising utilizing a computer to store data concerning said structural integrity data and at least one of said movement or position of the eddy current probe.

3. A method in accordance with claim 2 further comprising analyzing said stored data after completion of said storing of data to determine positions of structural integrity defects on the metallic post.

4. A method in accordance with claim 1 wherein said metallic post is a dovetail post of a turbine engine.

5. A method in accordance with claim 4 wherein the inspection is performed during a hot gas path outage.

6. A method for inspecting a metallic post that is contoured in a single dimension for defects, said method comprising:
   clamping an eddy current probe having at least one jaw with a surface conforming to the contour to the metallic post, said at least one jaw also having a plurality of eddy current coils and said sensor having at least one rubber wheel configured to move the eddy current probe along the metallic post;
   operating the eddy current probe while clamped to produce data relating to structural integrity of the metallic post; and
   moving the eddy current probe along the post using the rubber wheel while clamped and while sensing said structural integrity data.

7. A method in accordance with claim 6 further comprising sensing at at least one of movement or position of the eddy current probe.

8. A method in accordance with claim 6 further comprising accurately controlling movement of the eddy current probe.

9. A method in accordance with claim 6 further comprising utilizing a computer to store data concerning said structural integrity data and at least one of said movement or position of the eddy current probe.

10. A method in accordance with claim 9 further comprising analyzing said stored data after completion of said storing of data to determine positions of structural integrity defects on the metallic post.

11. A method in accordance with claim 6 wherein said metallic post is a dovetail post of a turbine engine.

12. A method in accordance with claim 11 wherein the inspection is performed during a hot gas path outage.

13. An apparatus for inspecting a metallic post contoured in a single dimension for defects, said apparatus comprising a clamp having at least one jaw with a surface conforming to the contour to the metallic post, said at least one jaw also having a plurality of eddy current coils and said probe having at least one sensor configured to sense at least one of position or motion.

14. An apparatus in accordance with claim 13 further comprising a computer, and said clamp configured to transmit data from said eddy current coils and from said sensor configured to sense at least one of position or motion to said computer.

15. An apparatus in accordance with claim 14 wherein said computer is configured to analyze said transmitted data to determine locations of defects in the metallic post.

16. An apparatus in accordance with claim 14 having a storage device configured to store said transmitted data, and said computer further configured to analyze said stored data to determine locations of defects in a metallic post after said metallic post has been inspected.

17. An apparatus in accordance with claim 13 wherein said at least one jaw conforms in shape to a matching dovetail post of a turbine engine.

18. An apparatus for inspecting a metallic post contoured in a single dimension for defects, said apparatus comprising a clamp having at least one jaw with a surface conforming to the contour to the metallic post, said at least one jaw also having a plurality of eddy current coils and said probe having at least one motorized wheel configured to accurately move said clamp along said metallic post while clamped thereto.

19. An apparatus in accordance with claim 18 further comprising a computer, and said clamp configured to transmit data from said eddy current coils to the computer, and said computer configured to control said at least one motorized wheel and to record a position of said clamp on said metallic post.

20. An apparatus in accordance with claim 19 wherein said computer is configured to analyze said transmitted data to determine locations of defects in the metallic post.

21. An apparatus in accordance with claim 20 having a storage device configured to store said transmitted data, and said computer further configured to analyze said stored data to determine locations of defects in a metallic post after said metallic post has been inspected.

22. An apparatus in accordance with claim 18 wherein said at least one jaw conforms in shape to a matching dovetail post of a turbine engine.

* * * * *